(12) United States Patent      (10) Patent No.:   US 12,673,248 B2

Castillo Garcia                (45) Date of Patent:       Jul. 7, 2026

---

(54) ROBOTIC PLATFORM FOR HIPPOTHERAPY AND METHOD FOR MOTOR AND COGNITIVE ASSESSMENT AND STIMULATION

(71) Applicant: UNIVERSIDAD SANTIAGO DE CALI, Cali (CO)

(72) Inventor: Javier Ferney Castillo Garcia, Cali (CO)

(73) Assignee: UNIVERSIDAD SANTIAGO DE CALI, Cali (CO)

( * ) Notice: Subject to any disclaimer, the term of this patent is extended or adjusted under 35 U.S.C. 154(b) by 0 days.

(21) Appl. No.: 17/610,059

(22) PCT Filed: Apr. 16, 2021

(86) PCT No.: PCT/IB2021/053179

§ 371 (c)(1),
(2) Date: Nov. 9, 2021

(87) PCT Pub. No.: WO2021/260448

PCT Pub. Date: Dec. 30, 2021

(65) Prior Publication Data

US 2023/0285824 A1     Sep. 14, 2023

Related U.S. Application Data

(60) Provisional application No. 63/116,794, filed on Nov. 20, 2020.

(51) Int. Cl.
A63B 69/04       (2006.01)
A61B 5/11        (2006.01)

(52) U.S. Cl.
CPC ............ A63B 69/04 (2013.01); A61B 5/1116 (2013.01); *A61B 2562/0219* (2013.01);
(Continued)

(58) Field of Classification Search
CPC ........ A63G 19/20; A63B 71/04; A63B 69/04; A63B 69/0068; A63B 2244/24;
(Continued)

(56) References Cited

U.S. PATENT DOCUMENTS 4,988,300 A  *   1/1991   Yamaguchi ............ A63B 69/04
                                         472/99
6,616,456 B1  *   9/2003   Nalty ..................... A63B 69/04
                                         472/59

(Continued)

FOREIGN PATENT DOCUMENTS

BR      PI0904897 A2 *   4/2011
CN      110037709 A *   7/2019
(Continued)

OTHER PUBLICATIONS

English Machine Translation of RU-2423095-C2 provided by PE2E (Year: 2011).*

(Continued)

*Primary Examiner* — Joseph D. Boecker
*Assistant Examiner* — Brian T Khong
(74) *Attorney, Agent, or Firm* — Dinsmore & Shohl LLP

(57)            ABSTRACT

A cognitive assessment and stimulation method and a robotic platform for hippotherapy that comprises a structure comprising at least a high torque servomotor, and an articulated mechanism that simulates the horse's head, at least two load cells placed on the articulated mechanism of the structure, for controlling direction and speed, at least one seat module, that comprises at least one inertial sensor of posture intended to be placed on the patient to determine his/her posture, and one or more load cells placed on the seat to determine the load distribution thereon; and at least two pressure sensors for speed control and that further comprises a temperature control module, which allows temperature (Continued)

control, a visual stimulation sub-module and/or an auditory stimulation sub-module, a crane type module coupled to a harness comprising some stirrups which allow the transfer of the patient and also providing control of weight on the platform and give security to the patient, avoiding the risk of falling.

17 Claims, 6 Drawing Sheets

(52) U.S. Cl.
CPC ................. *A61B 2562/0247* (2013.01); *A61B 2562/0252* (2013.01); *A61B 2562/0271* (2013.01); *A61H 2201/1661* (2013.01)

(58) Field of Classification Search
CPC ............ A63B 2208/12; A63B 2220/52; A63B 26/003; G09B 9/00; A61B 5/1116; A61B 5/4561; A47C 31/126
See application file for complete search history.

(56) References Cited

U.S. PATENT DOCUMENTS

| | | | | |
|---|---|---|---|---|
| 2010/0125024 | A1* | 5/2010 | Nakano | .................. A63B 22/16 |
| | | | | 482/4 |
| 2011/0275939 | A1* | 11/2011 | Walsh | .................. G09B 19/003 |
| | | | | 434/257 |

| | | | | |
|---|---|---|---|---|
| 2015/0196821 | A1* | 7/2015 | Kang | ................. G09B 19/0038 |
| | | | | 434/247 |
| 2016/0030827 | A1* | 2/2016 | Greenwood | ....... G09B 19/0038 |
| | | | | 434/247 |
| 2016/0089059 | A1* | 3/2016 | Hu | ........................ A61B 5/7207 |
| | | | | 600/595 |
| 2019/0159952 | A1* | 5/2019 | Keibel | ............... A63B 24/0087 |
| 2019/0232113 | A1* | 8/2019 | Zets | ...................... A61B 5/1128 |

FOREIGN PATENT DOCUMENTS

| | | | | |
|---|---|---|---|---|
| JP | H09190871 | A | * | 7/1997 |
| JP | 2005111153 | A | * | 4/2005 |
| JP | 2012196310 | A | * | 10/2012 |
| KR | 101786367 | B1 | * | 11/2017 |
| RU | 2423095 | C2 | * | 7/2011 |

OTHER PUBLICATIONS

English Machine Translation of CN-110037709-A provided by PE2E (Year: 2019).*
English Machine Translation of JP-2012196310-A provided by PE2E (Year: 2012).*
English Machine Translation of JP H09190871 A provided by PE2E (Year: 1997).*
English Machine Translation of JP-2005111153-A provided by PE2E (Year: 2005).*
English Machine Translation of KR 101786367 B1 provided by Espacenet (Year: 2017).*
English Machine Translation of BRPI0904897A2 provided by Espacenet (Year: 2011).*

* cited by examiner

ROBOTIC PLATFORM FOR HIPPOTHERAPY AND METHOD FOR MOTOR AND COGNITIVE ASSESSMENT AND STIMULATION

CROSS-REFERENCE TO RELATED APPLICATIONS

This application is a U.S. National Phase of PCT/IB2021/053179, entitled "ROBOTIC PLATFORM FOR HIPPO-THERAPY AND METHOD FOR MOTOR AND COGNI-TIVE ASSESSMENT AND STIMULATION" and filed Apr. 16, 2021, which claims the priority benefit of U.S. Provisional Application No. 63/116,794 filed Nov. 20, 2020, both of which are hereby incorporated herein by reference in their respective entireties.

OBJECT OF THE INVENTION

This invention refers, in general, to a platform and methods for motor, cognitive and sensory rehabilitation, by the use of hippotherapy provided by a robotic platform.

One object of the invention is to provide a robotic platform suitable for hippotherapy that allows the assessment, safe and efficient treatment of motor and cognitive problems in disabled patients.

Likewise, another object of the invention is to provide a method for cognitive and motor assessment and stimulation by hippotherapy using the robotic platform, which allows significant improvements in convenience, safety, and efficacy of the method.

BACKGROUND OF THE INVENTION

Hippotherapy means treatment with the aid of a horse. In this type of treatment, a physiotherapist, making use of a specialized horse and a horse trainer, integrates the horse's movement in a type of therapy.

Hippotherapy also provides a dynamic support basis, allowing patients to improve their balance, control, and strength of their trunk. At the same time, it facilitates neuronal activity, vestibular stimulation, proprioceptive stimulation and psychosomatic influence.

Hippotherapy may treat different medical conditions, such as: autism spectrum disorder, substance abuse, multiple sclerosis, muscle dystrophy, amputation, mental development disorders, spinal cord injury, brain injury, brain palsy, seizure disorders, visual, auditory disability, learning disorders, emotional problems, anxiety disorders, behavioral problems, among others.

Hippotherapy has a great effect on different fields, such as cognitive field. In the case of persons that do not show a cognitive impairment associated to a disease, the object of cognitive stimulation (cognitive training) is to achieve stimulation, improvement and optimum functioning of important cognitive skills, to achieve a better well-being and personal autonomy, self-esteem and auto-efficiency, as well as the acquisition of skills necessary to satisfactorily confront emotional stress and instability situations. If the person has a cognitive impairment, cognitive stimulation favors the recovery and restoration of altered functions, slowing the impairment and achieving greater functional autonomy for a longer period.

In the field of communication, hippotherapy allows an improvement in gestural and oral communication. In the psychomotor field, it allows the development of horizontal and vertical position, the construction of body symmetry, promotes gross and fine psychomotor coordination, thus helping in the development of laterality. At the same time, it allows the acquisition of new techniques in horseback riding, such as getting on and off the horse, learning to ride the horse at walk, trot, and gallop.

Hippotherapy has an effect on the stimulation of peristalsis, stimulation of circulatory system and stimulation of the respiratory system. It also allows the regulation of muscle tone, inhibition of tonic reflexes and associated movements, the recording and automation of locomotion pattern, stabilization of trunk and head, an increase in elasticity, agility, muscle strength, and the development of proprioceptive system.

However, as animals are used in hippotherapy during application, this involves risks for both patient and therapist. At the same time, it is difficult to measure any variable on the animal. Likewise, it is difficult to replicate and quantify movements generated by the animal and the heat irradiated to the patient.

The horse moves tridimensionally, therefore, it moves horizontally, vertically and circularly. These movements generate stimuli on the patient's body that are focused on the hip, which at the same time affects the spine, pelvis and spinal cord.

In order to perform this therapy, the horse should be peaceful, docile, agile, receptive and have crossed trout, leading to difficulties in providing adequate means.

The horse performs three main movements that allow the use of hippotherapy. A first movement is abduction, which is observed in the frontal plane. The horse initiates its gait by lifting its lumbar muscles vertically, causing the patient to also rise vertically, which affects the pelvis, which performs lateral movements. By moving his/her pelvis sidewise, the patient seeks to stabilize his/her spine.

A second movement is extension-flexion, which is observed in the sagittal plane. In this movement, the horse moves its forelegs and pushes its hind legs at the same time, transmitting the gravity point from the back to the gravity center of the rider. Pelvis extends and rhythmically recovers, which results in extension-flexion on this area of the body.

A third movement is interexternal rotation, which is observed in the cross-sectional plane. In this movement, the horse moves forward its forelegs and folds its hind legs, causing the ventral muscles to make a contraction-extension movement. The pelvis of the patient responds with a circular rotation giving internal and external extensions of the pelvis and femoral heads at the acetabulum.

Thus, hippotherapy achieves the correction of posture triggering reference and error signals that are used to keep posture and balance. These signals consist of identifying when to gait and when not to do it.

On the other hand, the heat of the horse is a primary aspect in hippotherapy, and it is also one of the characteristics of rehabilitation which is more difficult to simulate in robotic platforms.

In prior art, there are some robots that try to emulate the horse's movement and some sensors and actuators to measure and move said robots.

There are different solutions in the field of robotic rehabilitation for occupational therapy and physiotherapy. Technologies based on rehabilitation robotics promote inclusion and growth of potentialities of disabled populations, promoting cognitive and physical rehabilitation of children with special conditions.

There are solutions of platforms for motor control and learning based on hippotherapy simulator-type solutions which aim to achieve similar accelerations between the robot and real horse. In particular, solutions of systems with 6 degrees of freedom for hippotherapy that perform basic maneuvers of walking, trotting, galloping, and in which the horse rider can control the behavior of the simulator through sensors and an interactive interphase have been proposed.

However, no devices have been found in the state of the art that work on the interaction of the patient with the robot to improve some cognitive aspects and learning skills, and a system to improve the sitting posture and muscles in children with disabilities.

Likewise, in most cases, problems inherent to the intervention of animals in therapies are still there, such as the risks they imply and the low capacity to perform a quantitative assessment.

DESCRIPTION OF THE INVENTION

The invention refers to a robotic platform that integrates different modules to allow motor and cognitive rehabilitation.

The platform of the invention comprises:

A structure, that allows to emulate rotation and translation movements of the spine of the horse, in the three axis, and having 6 degrees of freedom. The structure comprises two high torque servomotors, and an articulated mechanism simulating the head of a horse.

At least two load cells located in the articulated mechanism of the structure, to control the movements of the articulated mechanism and speed reduction.

At least one seat module, comprising at least one inertial sensor of posture aimed to be placed on the patient to determine his/her posture, and one or more load cells situated on the seat to determine the load distribution thereon, thus obtaining a strength vector that is related to weight distribution of patient.

At least two pressure sensors for controlling speed.

Preferably, the sitting system has a temperature control module, with one or more temperature sensors, that allow for the control of temperature. The temperature control module comprises a thermal coating that emulates the temperature of the horse by means of a control system that regulates the temperature from 38° C. to 42° C. as a function of work speed.

The temperature control allows muscles of the lower part of the body of the patients to relax and distend.

More preferably, the sitting system comprises a nichrome wire frame coated with silicone, controlled by a solid-state relay and a microcontroller with a proportional, integral and derivative (PID) control based on an internal control model (ICM).

Thus, the therapist may control the heat irradiated by the temperature control module setting up the desired parameters. The heat of the horse is a primary aspect of hippotherapy and is also one of the most difficult rehabilitation characteristics to simulate in robotic platforms, wherein, in agreement with the horse's gait, heat is transferred to the rider, thus considerably improving all the stimuli of the pelvic belt and the spinal cord of the person, used to distend and relax the muscles, stimulate the tactile sensorial perception and improve blood flow stimulating the circulatory system, which benefits, in general, the physiological function of internal organs.

Additionally, the robotic platform may comprise a crane module that reduces the patient's body weight and gradually allows the positioning of the patient in the suitable posture on the platform. The crane module may be connected to the patient by means of a harness that may further comprise some stirrups. Thus, the stirrups allow the transfer of patients with low leg mobility to the platform. Also, in the case of patients with difficulty of postural control, the crane and the harness provide weight control on the platform and give security to the patient thus avoiding the risk of fall.

At least one seat module may comprise a plurality of inertial sensors intended to be located on the head, cervical vertebrae, lumbar vertebrae and on the hip of the patient, in order to examine the lateral movement of the whole trunk segment. Thus, it is possible to measure the posture of body segments of patients in order to evaluate the weight distribution of patients.

With the same purpose, the at least one seat module may comprise at least three load cells to determine the patient's location, by calculating the resultant determinant between one load cell and the other, the patient's total weight and a strength vector at the platform in the combination of a load distribution system located under the platform seat.

Preferably, the seat module may further comprise a visual stimulation sub-module connected to the load cells in order to indicate the patient's position and a correction of patient's body location by visual stimuli. Preferably, the visual stimulation sub-module comprises a RGB LED ring indicating weight distribution by means of colors in the direction in which the patient's body is located.

The RGB LED ring, depending on the posture and the distribution of the patient's weight activates a set of LEDs of different colors in the direction in which the patient is located, informing on the need to correct the location of his/her body on the platform, improving the patient's proprioception on suitable posture and the distribution of the weight on the robot. The LED ring may comprise, preferably, three LEDs indicating the intensity with which the patient's weight distribution deviates in one direction, being green colored when the intensity is low, yellow colored when the intensity is medium and red colored when the intensity is high.

Alternatively, the visual stimulation sub-module comprises a screen with color sequences indicating the weight distribution by means of colors.

The seat module may further comprise an auditory stimulation sub-module that comprises a player and a speaker to indicate corrective actions to the patient. Preferably, the auditory stimuli are achieved with an mp3 module and the signal is amplified and reproduced by a speaker.

Sound stimuli are activated to identify the horse's speeds when the motor functionality is used; when cognitive functions are assessed, it generates tones or a sequence of tones that are associated to orders or instructions such as increasing speed or performing any lateral movement of the horse's neck.

The stimuli to the patient are used to indicate the actions of increasing or reducing the platform speed or turning right or left.

The therapist may program visual stimuli to evaluate any executive function in patient and each color or color sequence to evaluate the response of the child to speed, the inhibition function or the follow up instructions. The led ring located in front of the patient may be programmed to generate visual stimuli to the patient, which functions with single series communication protocol which means that each color corresponds to a signal.

The platform of the invention may further comprise a processing module connected to the rest of the elements of the platform to configure its functioning, and a communication module that connects the processing module with the rest of the elements of the platform.

The invention also refers to a cognitive and motor assessment and stimulation method using a described robotic platform and that comprises the steps of:

defining a set of functioning parameters of the robotic platform;

initiating a movement on the robotic platform;

receiving a control signal from the patient, by means of pressure sensors or from the load cells placed on the articulated mechanism of the structure;

determining the direction and speed set by the patient in relation to the received control signal;

determining the patient's posture in relation to a signal coming from the inertial sensors of the seat module;

determine the patient load distribution on the seat by means of a signal coming from the load cells situated on the seat;

calculating a movement required to correct the patient's posture, by means of the processing module;

physically, visually or auditorily stimulating the patient to correct his/her posture, by means of the crane module, the visual stimulation module and/or the auditory stimulation module.

The method of the invention may further comprise a step of controlling the temperature on the seat module by means of the temperature control module by setting a temperature between 38° C. and 42° C., which is variable to simulate the heat transfer from the body of a horse.

The structure of the platform may be designed as a parallel robot with Gough-Stewart-type design.

The structure of the platform allows to emulate the movements of the horse, and the therapist may decide how many degrees of yaw, pitch and roll, how much distance in x, y, z or the suitable level of intensity (walk, trot and gallop) needed by the patient in the assessment.

The platform of the invention has the functionality of cognitive stimulation of the patient as it allows to evaluate certain executive functions related to learning and experience processes of the child.

The platform of the invention allows to carry out effectively hippotherapy at a lower cost and with greater comfort, both for users and for the physiotherapist, generating movements that are effective to help in patient's recovery.

The proposed platform also allows therapy by means of hippotherapy in many areas, thus allowing the cognitive and motor assessment in persons with disabilities.

The designed platform also has functionalities aimed to motor rehabilitation, by means of the emulation of equine movements, cognitive development and combination of both, by improving proprioception therefore stimulating the patient to sit correctly on the platform and preserve his/her postural location.

DESCRIPTION OF THE DRAWINGS

In order to complete the description being embodied and with the object of helping to a better understanding of the features of the invention, according to a preferable embodiment example thereof, a set of drawings is included as part of said description, which are for illustrative and not limiting purposes, as follows.

PREFERRED EMBODIMENT OF INVENTION

Figure 1:
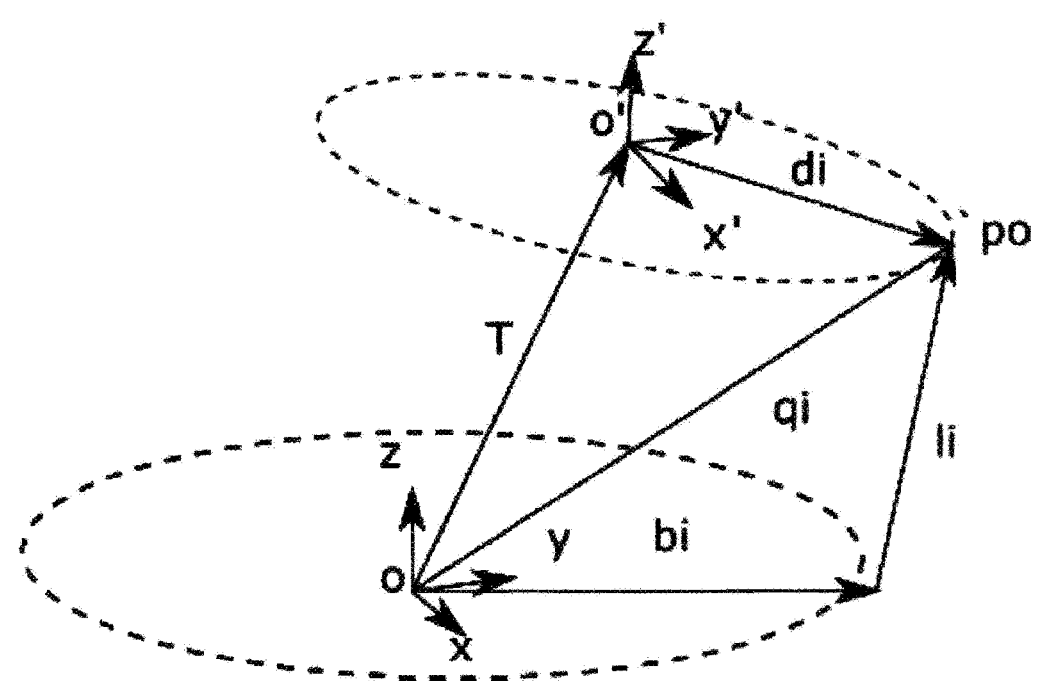
FIG. 1.—depicts a scheme of the coordinates of a Gough-Stewart platform.

The invention is a robotic platform to imitate hippotherapy and which is able to detect the patient's posture through load distribution and reduce body weight.

The robotic platform for hippotherapy of the invention comprises, in a particular embodiment, a structure (1) with 8 high torque servomotors (2) ASMB04B with a direct current working voltage 11-24V, a maximum torque of 380 kg*cm and a maximum rotation angle of 300° (±150° or from 0° to −300°).

The platform also comprises an articulated mechanism (3) that simulates the head of the horse, at least two load cells (4) located in the articulated mechanism (3) of the structure (1), for the control of direction and speed, and at least two pressure sensors (11) for the control of speed.

The platform comprises at least one seat module (5), comprising inertial sensors (6) MPU6050-GY521 of posture intended to be placed on the patient, to determine his/her posture. Sensors (6) MPU6050-GY521 are an inertial measuring unit (IMU) of six degrees of freedom (6DOF), combining a 3-axis accelerometer and a 3-axis gyroscope.

This sensor (6) plays an important role since, in addition to monitoring the patient's posture, it allows to record the seat orientation.

The platform also comprises one or more load cells (7) located on the seat (5) to determine the load distribution thereon, which consist of strain gauges, that at the slightest change of strain in the resistance submitted to strains along with a HX 711 module converts the analog signal into a digital signal proportional to the cell deformation (7).

Figure 5:
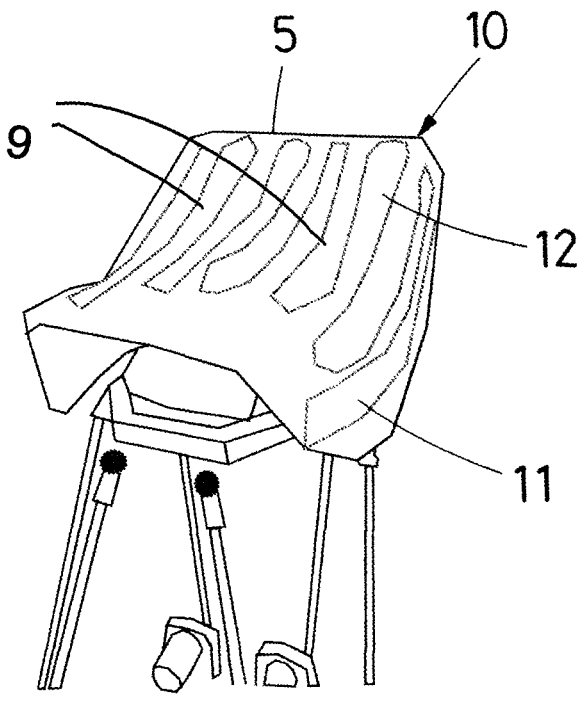
FIG. 5.—depicts a second view of a preferred embodiment of the platform of the invention that incorporates the temperature control module.

As shown in FIG. 5, the platform also comprises a temperature control module (10) which allows to control the temperature, that comprises a coating (12) of a nichrome wire frame coated with silicone, controlled by a solid state relay and a microcontroller with a proportional, integral and derivative (PID) control based on an internal control model (ICM). The temperature module has 2 different temperature sensors (9) in charge of obtaining the temperature of modes that emulate a horse in a resting, walking and trotting position, with temperatures from 38 to 42° C., respectively.

One of the sensors (11) along with a Solid State Relay, are in charge, by means of a proportional integral (PI) system, of controlling the heat generating system, transported by a nichrome string coated with silicone capable of withstanding temperatures of up to 55° C.

The platform also comprises a processing module connected to the rest of the platform elements to configure its functioning. The processing module is an Arduino® One and Mega 2560-type module, and is used for processing mathematic equations and creating tridimensional movements on the Stewart platform, the movement of the articulated movement (3) that simulates the head and neck, the temperature control processing, the data collection from inertial sensors (6) MPU6050, the RGB LED ring control (15) and the control of load cells (7) and the orders from the pressure sensors (11) (FSR402).

The platform comprises a communication module that connects the processing module with the rest of the elements of the platform. Communication is possible via SPI as well as via the 12C bus, using a multiplexor 12C, therefore it is easy to obtain the measured data.

The platform has two power sources S-400 of 24 volts and 16.6 amperes each.

The platform is developed using the solution to the mathematic problem of a Gough-Stewart platform. Thus, real structure data (1) are calculated and implemented in an algorithm in charge of the mobility of servomotors (2). FIG. 1 depicts the coordinates of a Stewart platform, between a base (bottom) and a platform (top).

By using this approach, 40 possible solutions were found, even though in practice many of the solutions would not be useful, and therefore it was decided to select rotating servomotors (2) instead of linear ones, to reduce the complexity of implementation.

The servomotors (2) allow for the incorporation of the 3 movements of different planes in one, being the therapist the one who decides how many degrees of yaw, pitch and roll or how much distance in x, y, z the patient needs in the current state of his/her examination together with the 3 intensity levels (walking, trotting and galloping).

In traditional hippotherapy, the horse should meet certain requirements such as its walk, size, height, temperature and age, while the use of a Stewart platform solves these requirements with a standard model based on mathematic and programming solutions. In traditional hippotherapy, the ground also has a strong influence because it should be flat, instead, as regards the structure, there is no need for an off-site clinic environment.

The platform is designed with an Arduino® microcontroller, which offers the therapist a menu with which he should enter the corresponding values in position of x, y, z and the rotation angles of axes x, y, z (yaw, pitch and roll) for the current stage of the patient along with the suitable level of intensity therefore.

At any moment of the therapy, the therapist is free to change the parameters in order to improve the result reflected on the patient and seek for better results.

In the implementation of temperature control, once the model is obtained (internal resistance of the nichrome wire) and the controller designed for the platform, it is possible to apply different adjustment methods of the controller, such as the Ziegler Nichols method, the Cohen Coon method or the internal control model (ICM) among others, that are used to meet the requirements of temperature control of the system.

In order to compensate the controller, gains of each one of control actions should be adjusted in order to obtain an acceptable response of the process variable. Adjustment methods for proportional, integral and derivative controllers determine the adjustment of the system requirements, such as gain, derived time and integral time. In the controller tuning, the process dynamics should be first identified, then the controller tuning method is selected and from this response, the parameters of the controller to be implemented are determined.

Since there is the mathematical inverse of the operator describing the platform, this inverse is used as the controller and the closed circuit system is stable with this controller. The internal control model has been used as a control strategy that gives excellent results, thanks to its robustness in the presence of disturbances caused in the system.

The control by the internal model directly depends on the system structure and its mathematical model, this method consists of designing the controller according to the system requirements. In order to apply this adjustment method, the platform should be tested to see how it responds. From this response, the design parameters are chosen, with these parameters, the controller is designed and, finally, this controller is applied to the plant in order to see its response. In this case, the solution is focused on first order models plus delay time.

Figure 2:
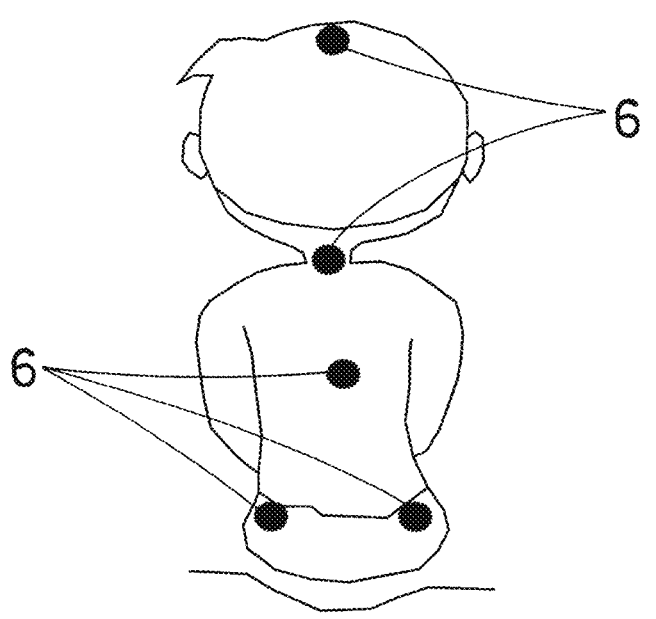
FIG. 2.—depicts the placement of inertial sensors on the body of a patient in an embodiment of the invention.

In a particular embodiment, the platform comprises a crane module (13), which also comprises a harness (17) adjusted to the patient's body, placing the sensors (6) as shown in FIG. 2 and placing them: one on the head, another one on the cervical vertebrae, another one on the lumbar vertebrae and two on the hip, in order to examine the lateral movement of the whole trunk segment.

Figure 3:
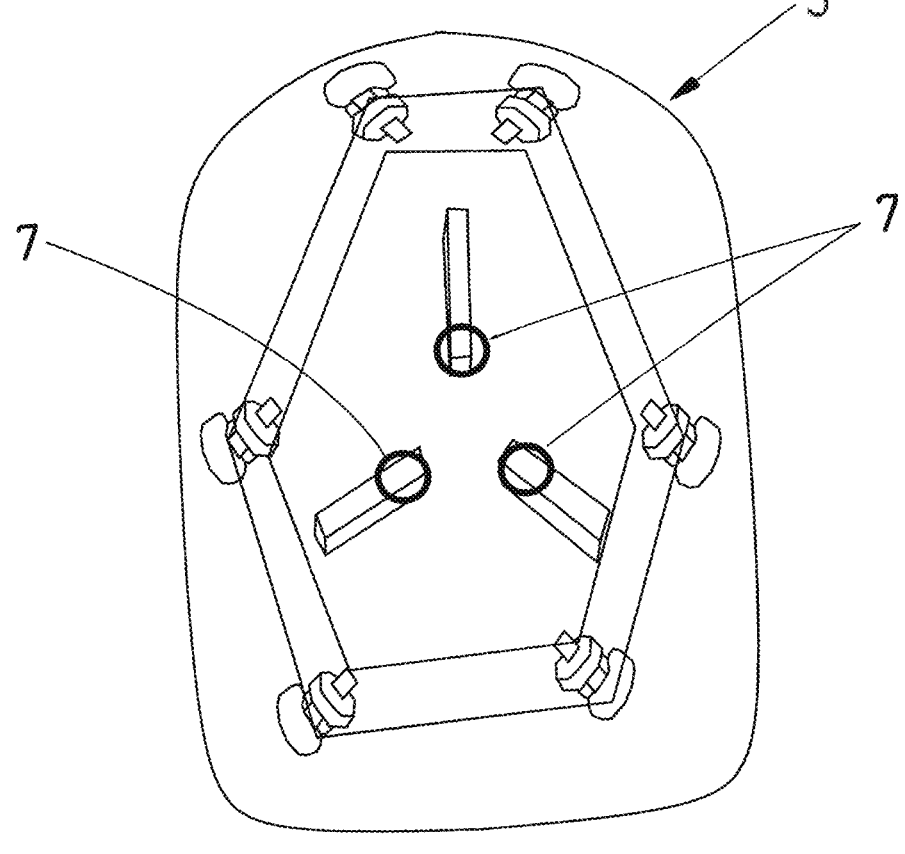
FIG. 3.—depicts three load cells that allow to determine the location of the patient on the seat module in an embodiment of the invention.

In the determination of the sitting position, in this case, the platform comprises 3 load cells (7) ELN0418 with their respective modules HX711. FIG. 3 shows three load cells (7) that allow for the determination of patient's location on the seat module (5) using the calculation resulting from one load cell and the other.

The location of patient on the seat (5) of the platform is shown by means of a ring (15) with 24 programmable RGB LEDs, which is powered with 5 volts and is commanded by a PWM signal of the microcontroller, which, depending on the patient's location will light a color in the direction it is placed, therefore informing the patient to correct the location of his/her body on the structure.

Other two load cells (4) are placed on the articulated mechanism (3) of the structure (1) to instruct the servomotors (2) of head and neck, therefore determining the stop and direction of structure (1). This movement is commanded by a microcontroller ATMEGA16u2, which is in charge of sending the PWM signal to each servomotor (2). In order to increase the structure speed, pressure sensors (11) FSR402 were used.

Figure 7:
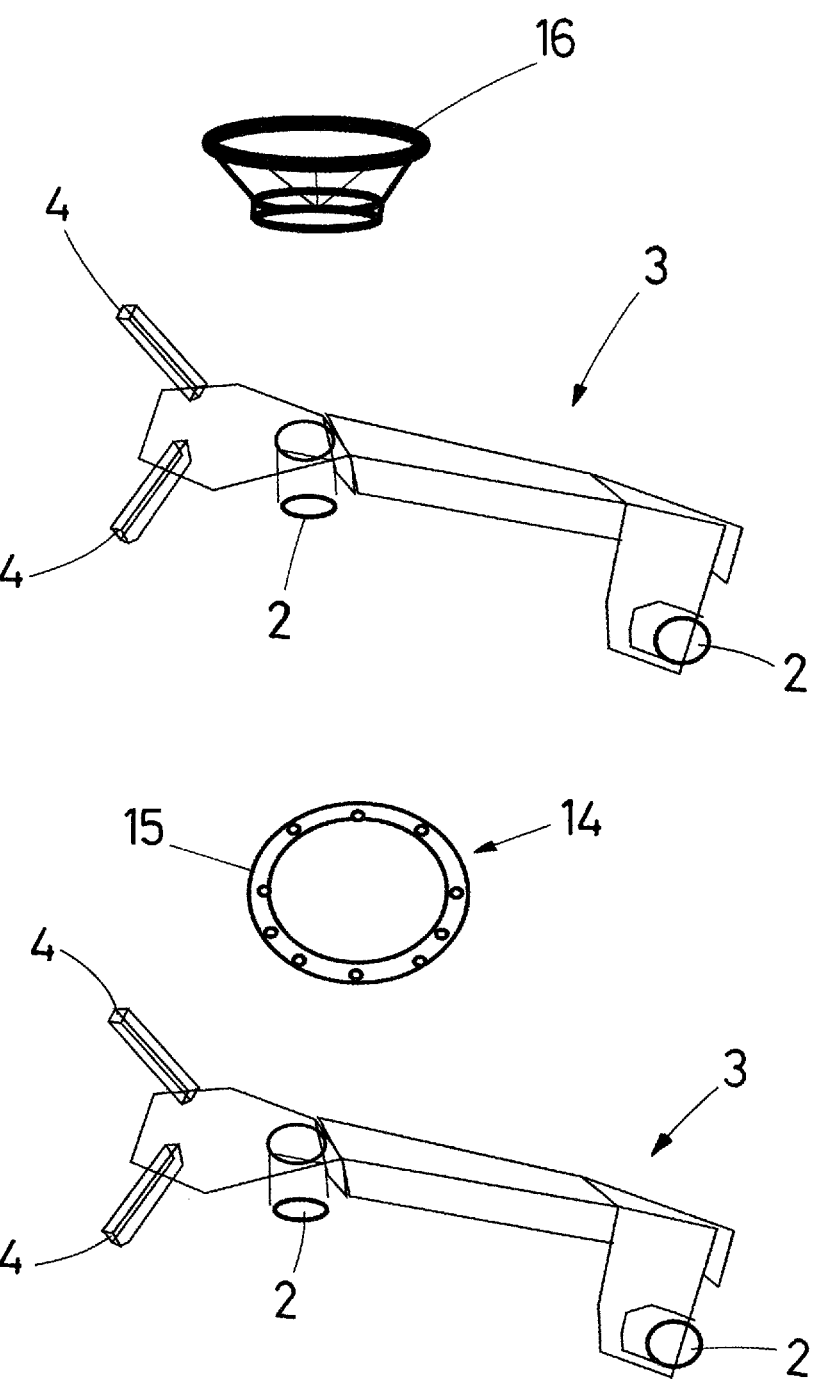
FIG. 7.—depicts a view of the visual and auditory stimulation module in an embodiment of the invention.

As shown in FIG. 7, LED ring (15) used to determine the location of the patient was also programmed to be used in visual stimuli, which function with a serial communication protocol of one line, meaning that each color corresponds to a signal. The auditory stimuli are achieved with an mp3 module and the signal is amplified and reproduced by a speaker.

Figure 8:
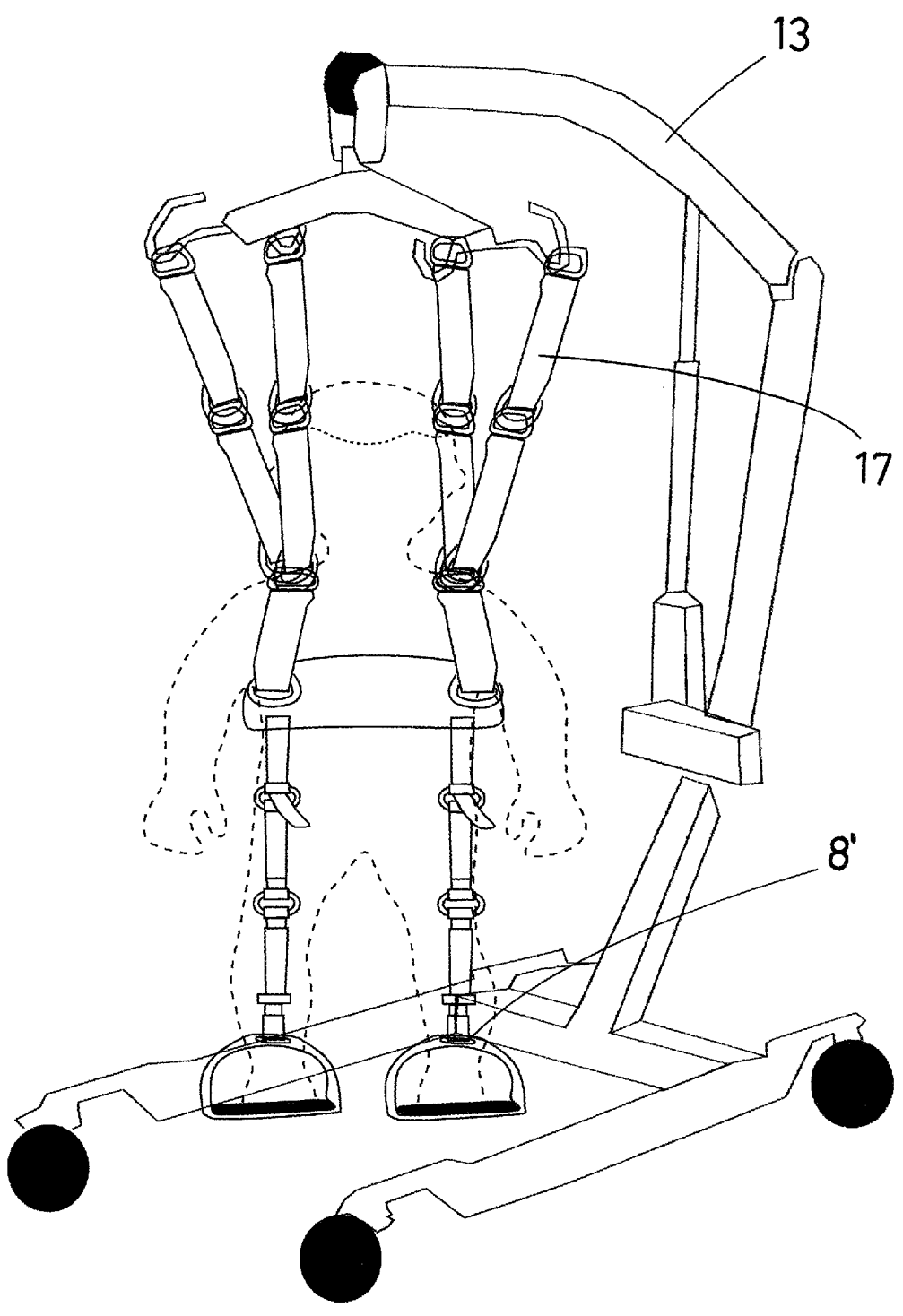
FIG. 8.—depicts a view of the crane module with harness and stirrups in an embodiment of the invention.

FIG. 8 shows an embodiment of the crane module (13) of the platform of the invention, which also comprises a harness (17) to hold patient and two stirrups (8) to hold his/her legs.

Figure 4:
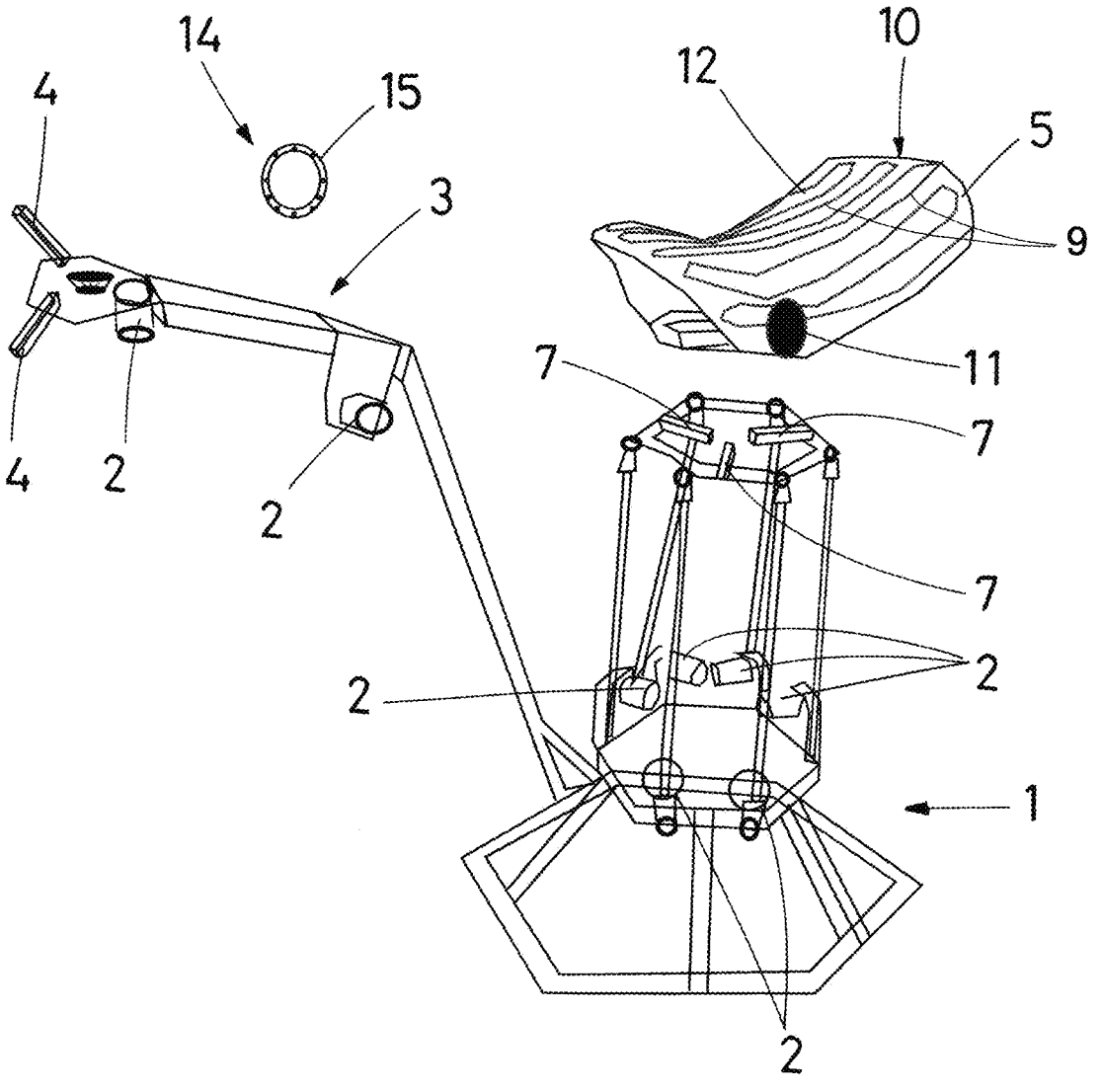
FIG. 4.—depicts a scheme of a preferred embodiment of the platform of the invention.

FIG. 4 shows an embodiment of design and implementation of the robotic platform for hippotherapy.

The movements performed by the platform emulate the therapeutic movements for hippotherapy. Since there are no equations for modeling these movements, the precision with which the platform performed the rotational and translational movements in axes X, Y, Z was established.

TABLE 1

| Axis Z | Distance (cm) | | | | | | | | |
|---|---|---|---|---|---|---|---|---|---|
| | 0 | 2 | 4 | 6 | 8 | −2 | −4 | −6 | −8 |
| X (error %) | 4.1 | 2.3 | 1.6 | 4.0 | 2.2 | 2.0 | 3.3 | 2.0 | 4.1 |
| Y (error %) | 2.3 | 0.7 | 2.3 | 2.0 | 2.9 | 1.9 | 2.5 | 1.8 | 2.3 |
| Z (error %) | 5.2 | 1.7 | 4.5 | 4.7 | 1.4 | 3.7 | 0.6 | 1.5 | 5.2 |

Table 1 shows the error percentages regarding the 3 platform axes, being these error percentages lower than 5%, this is, compared with the low repeatability that may be achieved with a horse, a satisfactory result. These results were obtained using distance sensors located on the platform and performing different positions shown in table 1.

TABLE 2

| Axis | Angle (degrees) | |
| | Min (error %) | Max (error %) |
| --- | --- | --- |
| X (error %) | −5° (9.4) | 7° (8.7) |
| Y (error %) | −10° (5.3) | 10° (7.6) |
| Z (error %) | −20° (11.2) | 20° (9.8) |

Table 2 shows the error percentages obtained for minimum and maximum rotational movements for the three axes, the reading of the angle was obtained by acquiring an inertial sensor MPU6050 which is integrated to the platform.

The temperature control was implemented in an Arduino® microcontroller based on PID control (Proportional, Integral and Derivative Controller). This is a feedback controller, which calculates the deviation or error between a mean value and the desired value. The actuator is a solid state relay, which switches a load through a PWM (pulse width modulation) activation signal generated from the Arduino® microcontroller. The temperature sensor used was DS18B20.

TABLE 3

| Temperature (° C.) | Time (Seconds) |
| --- | --- |
| 29.3 | 122 |
| 33.6 | 205 |
| 37.9 | 298 |
| 42.2 | 396 |

Table 3 shows time and temperature measurement values for the open circuit heat generating system, the heat generating system is excited by a voltage of 4.3 v (DC) of PWM Arduino® and reaches the actuator (solid state relay) and heats the electric resistance of 110 v (AC). These data allow for the calculation of the equation of the first order transfer function that is better adapted to the data collected.

The controller adjustment process may be empirical or by using more elaborated techniques such as the Ziegler Nichols method, the Cohen Coon method or the internal control model (ICM), the PI controller yield rates implemented using the different yield techniques, are shown in table 4.

TABLE 4

| Methods | UAE | ISE | Mp | Ts/sec |
| --- | --- | --- | --- | --- |
| Empiric | 222.1535 | 135.4448 | 1.2 | 484 |
| Ziegler Nichols | 311.4675 | 135.4925 | 1.3 | 520 |
| Cohen Coon | 242.5618 | 122.3332 | 1.35 | 601 |
| ICM | 38.6743 | 39.9203 | 1.0 | 360 |

The tuning method by internal model is the one showing better results since it shows shorter set-up time, less exceedance, less dynamic error and less absolute error.

With the development of the platform, a general error rate was found of less than 10% of rotation and translation movements.

On the other hand, the seat (5) of the platform allows the evaluation and training of the patient's position, since it records the values of strength vector expressed by the angular value and the magnitude of the vector resulting from the strains present in the three load cells (7), located at the base of the seat module (5) and which output is sent and represented by a circular LED array (15).

Figure 6:
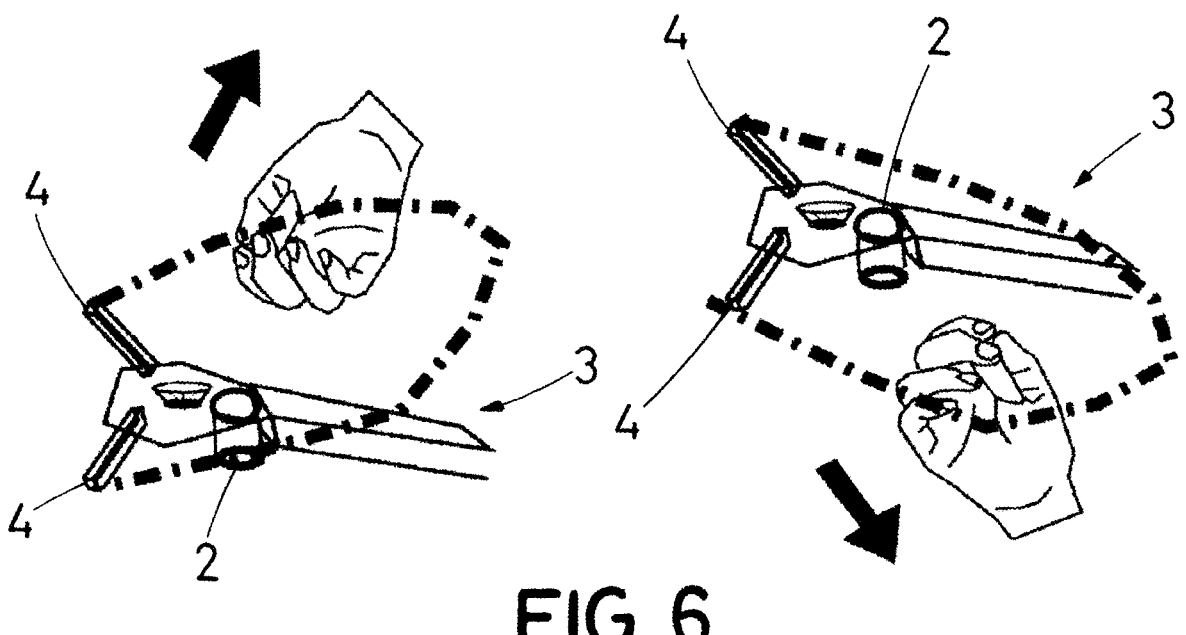
FIG. 6.—depicts a view of the articulated mechanism that simulates the neck and head of the horse in an embodiment of the invention.

The head and neck of the platform may be controlled to emulate the horse's movements, the control of the head rotation is achieved by the variation of two load cells (4) connected to reins, to apply more stress on one side than on the other, the platform turns the head, as shown in FIG. 6. When the pressure sensors (11) FSR402 are pressed, the system increases speed and when the same tension is applied to both sides of the reins, the system reduces the speed.

The proposed system has 3 functionalities, a motor function that works performing soft movements to stimulate the lumbar zone and hip; a cognitive function, that stimulates the patient to interact with his/her own hands through auditory and visual stimuli, and a motor and cognitive function which brings together all the capabilities offered by the platform, leading the patient to directly interact with the platform, being him/herself who makes the structure move always under safe conditions.

The invention claimed is:

1. A robotic platform for providing hippotherapy to a pediatric patient with a disability, the robotic platform comprising:

a structure comprising at least one high torque servomotor and an articulated mechanism simulating a head of a horse;

at least two load cells located in the articulated mechanism of the structure, for a control of direction and speed;

at least one seat module comprising:

a seat providing a sitting surface for the pediatric patient, at least one inertial sensor of posture configured to be disposed on one or more of a cervical vertebrae, a lumbar vertebrae, and a hip of the pediatric patient seated on the seat to determine a posture of the pediatric patient, the at least one inertial sensor of posture being an inertial measurement unit configured to provide measurements of movement in an x-axis, a y-axis, and a z-axis, three load cells arranged in a triangular pattern on the seat to determine a load distribution of the pediatric patient thereon, a visual stimulation sub-module comprising a RGB LED ring configured to emit light as one or more sequences or patterns of color toward the pediatric patient, and an auditory stimulation sub-module configured to emit one or more sequences of tones toward the pediatric patient; and at least two pressure sensors for a control of speed;

a crane module comprising a harness and a plurality of stirrups, the crane module supporting the pediatric patient via the harness and the plurality of stirrups to reduce a weight of the pediatric patient on the at least one seat module and to modify the posture of the pediatric patient; and a processing module communicatively coupled to the at least one high torque servomotor of the structure, the at least two load cells of the articulated mechanism, the at least one inertial sensor of posture, and the three load cells, the visual stimulation sub-module, and the auditory stimulation sub-module of the at least one seat module, the processing module configured to:

receive one or more inputs from a caregiver, the one or more inputs corresponding to a therapy protocol for evaluating an executive function of the pediatric patient, cause rotational movement of the structure in the x-axis, the y-axis, and the z-axis based on the determination of the posture and the load distribution of the pediatric patient in accordance with the therapy protocol, cause the visual stimulation sub-module to emit the light in a determined sequence and/or pattern based on the therapy protocol, the determined sequence and/or pattern eliciting responses from the pediatric patient that are indicative of the executive function of the pediatric patient, cause the auditory stimulation sub-module to emit a determined sequence of tones based on the therapy protocol, the determined sequence of tones eliciting responses from the pediatric patient that are indicative of the executive function of the pediatric patient, and adjust the rotational movement of the structure based on the responses from the pediatric patient and/or additional inputs received from the caregiver.

2. The robotic platform of claim 1, further comprising a temperature control module configured to sense a temperature of the pediatric patient at a point of contact with the sitting surface via one or more temperature sensors, and causing heating of the sitting surface to 38° C. and 42° C. based on the temperature of the pediatric patient to simulate a horse body temperature.

3. The robotic platform of claim 2, wherein the temperature control module comprises a coating of a nichrome wire frame coated with silicone, controlled by a solid state relay and a microcontroller with a proportional, integral and derivative (PID) control based on an internal control model (ICM).

4. The robotic platform of claim 1, wherein the visual stimulation sub-module is connected to the at least two load cells in order to indicate a position of the pediatric patient and a correction of a location of a body of the pediatric patient by visual stimuli.

5. The robotic platform of claim 4, wherein the visual stimulation sub-module comprises a screen with color sequences indicating the weight distribution.

6. The robotic platform of claim 1, wherein the auditory stimulation sub-module comprises a player and a speaker to emit the determined sequence of tones.

7. The robotic platform of claim 1, further comprising a bus coupled to the processing module, the at least one high torque servomotor of the structure, the at least two load cells of the articulated mechanism, the at least one inertial sensor of posture, and the three load cells of the at least one seat module.

8. The robotic platform of claim 1, wherein the light in the determined sequence and/or pattern is in a form of at least one color, wherein each color corresponds to a signal indicated to the pediatric patient and/or the caregiver.

9. The robotic platform of claim 1, wherein the RGB LED ring is a proprioception indicator and comprises a plurality of LEDs that each emit light at a predetermined color that corresponds to signals provided by the three load cells, the predetermined color indicating a deviation of weight distribution of the pediatric patient on the at least one seat module.

10. The robotic platform of claim 9, wherein the predetermined color is:

green when the signals received from the three load cells indicates a relative low intensity deviation in weight distribution;

yellow when the signals received from the three load cells indicates a relative intermediate intensity deviation in weight distribution; and red when the signals received from the three load cells indicate a relative high intensity deviation in weight distribution.

11. The robotic platform of claim 1, wherein the determined sequence of tones are associated with orders or instructions to adjust movement of the structure that is stimulating movement of the head of the horse.

12. The robotic platform of claim 1, wherein processing module is configured to adjust the rotational movement of the structure by adjusting an intensity and/or a degree of the rotational movement of the structure based on the executive function of the pediatric patient.

13. The robotic platform of claim 1, wherein the therapy protocol for evaluating the executive function of the pediatric patient comprises an executive function relating to learning and experience processes of the pediatric patient.

14. The robotic platform of claim 1, wherein:

the processing module is configured to cause rotational movement of the structure by causing soft movements to stimulate a lumbar zone and hips of the pediatric patient;

the processing module is further configured to initiate a cognitive function by causing the visual stimulation sub-module to emit the light and the auditory stimulation sub-module to emit the determined sequence of tones to elicit interaction of the pediatric patient with the robotic platform via hands of the pediatric patient; and causing the soft movements and initiating the cognitive function results in the pediatric patient moving in a manner that causes corresponding movement of the structure.

15. The robotic platform of claim 1, wherein the rotational movement of the structure, the light emitted by the visual stimulation sub-module, and the determined sequence of tones emitted by the auditory stimulation sub-module, together with sensed information from the at least two load cells and the at least two pressure sensors that are indicative of a response of the pediatric patient provides data usable for assessment and treatment of the pediatric patient.

16. A method for cognitive assessment and stimulation of a pediatric patient with a disability using a robotic platform, the method comprising:

defining a set of functioning parameters of the robotic platform, the robotic platform comprising:

a structure comprising at least one high torque servomotor and an articulated mechanism simulating a head of a horse, at least two load cells located in the articulated mechanism of the structure for a control of direction and speed, at least one seat module comprising a seat providing a sitting surface for a pediatric patient, at least one inertial sensor of posture configured to be disposed on one or more of a cervical vertebrae, a lumbar vertebrae, and a hip of the pediatric patient seated on the seat to determine a posture of the pediatric patient, three load cells arranged in a triangular pattern on the seat to determine a load distribution of the pediatric patient on the seat, a visual stimulation sub-module comprising a RGB LED ring configured to emit light as one or more sequences or patterns of color toward the pediatric patient, and an auditory stimulation sub-module configured to emit one or more sequences of tones toward the pediatric patient, the at least one inertial sensor of posture being an inertial measurement unit configured to provide measurements of movement in an x-axis, a y-axis, and a z-axis, at least two pressure sensors, and a crane module comprising a harness and a plurality of stirrups, the crane module supporting the pediatric patient via the harness and the plurality of stirrups to reduce a weight of the pediatric patient on the at least one seat module and to modify the posture of the pediatric patient;

receiving one or more inputs from a caregiver, the one or more inputs corresponding to a therapy protocol for evaluating an executive function of the pediatric patient;

initiating a movement on the robotic platform via the at least one high torque servomotor, the movement of the robotic platform comprising rotational movement in the x-axis, the y-axis, and the z-axis;

causing the visual stimulation sub-module to emit the light in a determined sequence and/or pattern based on the therapy protocol;

causing the auditory stimulation sub-module to emit a determined sequence of tones based on the therapy protocol;

receiving a control signal from the pediatric patient via the three load cells, wherein movement of the pediatric patient to generate the control signal is in response to the light and the determined sequence of tones and based on the executive function of the pediatric patient;

determining a direction and a speed set by the pediatric patient based on the received control signal;

determining a posture of the pediatric patient based on a signal coming from the at least one inertial sensor of the at least one seat module;

determining a distribution of a load of the pediatric patient on the at least one seat module via the three load cells;

calculating a movement required to correct the posture of the pediatric patient, via a processing module;

reducing the weight of the pediatric patient via the crane module; and physically stimulating the pediatric patient to correct his/her posture via the the visual stimulation sub-module and/or the auditory stimulation sub-module.

17. The method of claim 16, further comprising a step of controlling a temperature on the seat module via a temperature control module by setting the temperature between 38° C. and 42° C., and variable to simulate heat transfer from a body of a horse.

* * * * *